(12) United States Patent
Kastner

(10) Patent No.: US 10,576,676 B2
(45) Date of Patent: Mar. 3, 2020

(54) APPARATUS AND METHOD FOR MANUFACTURING AND TESTING WORKPIECES

(71) Applicant: Next Generation Analytics GmbH, Grieskirchen (AT)

(72) Inventor: Friedrich Kastner, Grieskirchen (AT)

(73) Assignee: Next Generation Analytics GmbH, Grieskirchen (AT)

( * ) Notice: Subject to any disclaimer, the term of this patent is extended or adjusted under 35 U.S.C. 154(b) by 413 days.

(21) Appl. No.: 15/509,890

(22) PCT Filed: Sep. 9, 2015

(86) PCT No.: PCT/AT2015/050219
§ 371 (c)(1),
(2) Date: Apr. 21, 2017

(87) PCT Pub. No.: WO2016/037206
PCT Pub. Date: Mar. 17, 2016

(65) Prior Publication Data
US 2017/0239870 A1    Aug. 24, 2017

(30) Foreign Application Priority Data

Sep. 10, 2014 (AT) .................................. 50624/2014
Dec. 17, 2014 (AT) .................................. 50920/2014

(51) Int. Cl.
*B29C 47/92* (2006.01)
*G01N 11/08* (2006.01)
(Continued)

(52) U.S. Cl.
CPC .............. *B29C 48/92* (2019.02); *B29B 7/428* (2013.01); *B29B 7/488* (2013.01); *B29B 7/582* (2013.01);
(Continued)

(58) Field of Classification Search
CPC ... B29C 48/92; B29C 48/6914; B29C 48/288; B29C 2948/92828; B29C 2948/92333; B29C 2948/92019; G01N 11/08; B29B 7/726; B29B 7/603; B29B 7/582; B29B 7/488; B29B 7/428; B29B 7/38
See application file for complete search history.

(56) References Cited

U.S. PATENT DOCUMENTS 3,918,869 A    11/1975   Van Der Ploeg
4,832,882 A     5/1989   Moylan
(Continued)

FOREIGN PATENT DOCUMENTS

CA    2 643 213  A1    8/2007
DE    24 06 686  A1    8/1974
(Continued)

OTHER PUBLICATIONS

International Search Report of PCT/AT2015/050219, dated Apr. 5, 2016.

*Primary Examiner* — Robert J Grun
(74) *Attorney, Agent, or Firm* — Collard & Roe, P.C.

(57) ABSTRACT

A method and an apparatus manufactures and tests workpieces. The apparatus is mountable on or includes a system for mixing or melting materials. The apparatus includes application units and a replacement system that is designed to automatically replace application units in respect of the position or function thereof.

15 Claims, 4 Drawing Sheets

(51) Int. Cl.

| | | |
|---|---|---|
| *B29B 7/72* | (2006.01) | |
| *B29C 47/68* | (2006.01) | |
| *B29C 47/10* | (2006.01) | |
| *B29B 7/60* | (2006.01) | |
| *B29C 48/92* | (2019.01) | |
| *B29C 48/285* | (2019.01) | |
| *B29C 48/691* | (2019.01) | |
| *B29B 7/42* | (2006.01) | |
| *B29B 7/48* | (2006.01) | |
| *B29B 7/58* | (2006.01) | |
| *B29B 7/38* | (2006.01) | |

(52) U.S. Cl.
CPC .............. *B29B 7/603* (2013.01); *B29B 7/726* (2013.01); *B29C 48/288* (2019.02); *B29C 48/6914* (2019.02); *G01N 11/08* (2013.01); *B29B 7/38* (2013.01); *B29C 2948/92019* (2019.02); *B29C 2948/92333* (2019.02); *B29C 2948/92828* (2019.02)

(56) References Cited

U.S. PATENT DOCUMENTS

| | | | |
|---|---|---|---|
| 4,955,550 A | 9/1990 | Satake et al. | |
| 5,148,943 A | 9/1992 | Moller | |
| 5,439,367 A | 8/1995 | Hehl | |
| 7,150,181 B2 | 12/2006 | Collin | |
| 2005/0017412 A1 | 1/2005 | Maier et al. | |
| 2006/0096696 A1 | 5/2006 | Oku et al. | |
| 2009/0115087 A1 | 5/2009 | Hellenberg et al. | |
| 2015/0290839 A1 | 10/2015 | Zang | |

FOREIGN PATENT DOCUMENTS

| | | |
|---|---|---|
| DE | 38 37 608 A1 | 5/1989 |
| DE | 42 19 885 A1 | 12/1992 |
| DE | 42 16 312 C1 | 11/1993 |
| DE | 100 18 321 A1 | 1/2001 |
| DE | 100 56 389 A1 | 5/2002 |
| DE | 101 50 796 A1 | 4/2003 |
| DE | 699 05 655 T2 | 11/2003 |
| DE | 10 2005 046 286 A1 | 3/2007 |
| DE | 10 2010 004 794 A1 | 8/2010 |
| DE | 10 2011 109 871 A1 | 1/2013 |
| DE | 10 2012 025 259 A1 | 6/2014 |
| EP | 1 550 543 A1 | 7/2005 |
| EP | 1 820 568 A1 | 8/2007 |
| EP | 2 551 659 A2 | 1/2013 |
| JP | S52-42553 A | 4/1977 |
| JP | S57-178734 A | 11/1982 |
| JP | S58-84742 A | 5/1983 |
| JP | S59-22711 A | 2/1984 |
| JP | S61-5908 A | 1/1986 |
| JP | H08-156072 A | 6/1996 |
| JP | 2002-036241 | 2/2002 |
| WO | 03/018287 A2 | 3/2003 |
| WO | 2006/103184 A1 | 10/2006 |

APPARATUS AND METHOD FOR MANUFACTURING AND TESTING WORKPIECES

CROSS REFERENCE TO RELATED APPLICATIONS

This application is the National Stage of PCT/AT2015/050219 filed on Sep. 9, 2015, which claims priority under 35 U.S.C. § 119 of Austrian Application No. A 50624/2014 filed on Sep. 10, 2014 and Austrian Application No. A 50920/2014 filed on Dec. 17, 2014, the disclosures of which are incorporated by reference. The international application under PCT article 21(2) was not published in English.

The invention relates to an apparatus for manufacturing and testing workpieces, in particular made from plastics.

The invention is particularly suitable for producing plastic. Accordingly, the term "material" as used below may be understood as meaning "plastic" in particular.

However, it is also possible to use the invention in other sectors which involve working with molten materials or mixtures. The term "material" when used in relation to these sectors may therefore also be construed differently, for example in the sense of "metal material" in the context of metal production or in the sense of "active ingredient" or "pharmaceutical substance" in the context of pharmaceutical production.

In the plastic manufacturing and processing industry, the purity and quality of many of the different types of plastic materials used can fluctuate sharply at times. A standardized method for determining material properties is the filter pressure test, which is the standard documented by DIN EN 13900-5 "Determination by filter pressure value test", for example.

FIG. 1 illustrates an apparatus for manufacturing plastic materials having a device for testing filter pressure known from the prior art which conforms to and defines an international standard for determining impurities (e.g. agglomerates) in plastics and similar media. A plastic material or a mixture of several plastic materials is introduced into the device via the illustrated hopper. By means of the device, a molten plastic is pressed through a defined filter module (e.g. a fabric filter or a screen) by an extruder, for example, and the increase in pressure which takes place upstream of the filter module when a defined quantity of material is extruded is recorded. This then serves as a measure of the dispersion quality or purity of the material because agglomerates, other non-molten particles and not sufficiently dispersed fillers, e.g. pigments, are held back by the filter module, which leads to an increase in pressure as material is continuously added to the filter module.

The disadvantage of the prior art is that after every individual measurement, the apparatus has to be rinsed, the hopper emptied if necessary and the filter manually replaced. This means that only one material can be tested at a time by an operator.

The objective of this invention was to overcome the disadvantages of the prior art and propose an apparatus and a method by means of which a user is able to work interchangeably with materials and/or workpieces, and in particular optimize the manufacture and/or material analysis of materials and/or workpieces, and more efficiently characterize purity using different filters (coarse, medium, fine, etc.).

This objective is achieved by an apparatus and a method as defined in the claims.

One special aspect of the invention is an apparatus and a method for testing the purity of a material melt (e.g. plastic melt) by pressing an exactly defined quantity of a melt through a filter module with defined characteristics whilst simultaneously measuring the melt pressure which builds up in front of the filter module. This is generally referred to as a "filter pressure test". Such an apparatus is also known as a "filter pressure test apparatus" and such a method as a "filter pressure test method".

Another special aspect of the invention is an apparatus and a method for the variable and in particular controlled manufacture of workpieces, in particular test samples with different properties made from variable materials and in variable material quantities. Such an apparatus is also known as a "metering apparatus" and such a method as a "metering method".

Based on a combination of the application apparatus with a filter pressure test apparatus, it is possible to produce workpieces of the highest quality under controlled conditions. At the same time, this opens up the possibility of conducting tests on various workpieces made from a range of different mixtures of materials without having to interrupt production to any noteworthy degree.

The apparatus for manufacturing and testing workpieces proposed by the invention is configured so that it can be mounted on a system for mixing or melting materials or comprises this system and is characterized by the fact that the apparatus comprises application units and a replacement system that is designed to automatically replace application units in respect of their position or their function.

Accordingly, the apparatus can be connected or is connected fixedly to the material inlet and/or material outlet of the system for mixing or melting materials in particular.

Application units are units by means of which something can be introduced into the manufacturing process. This might be materials used in this process on the one hand or alternatively modules for measuring the materials or products manufactured from the materials.

Depending on the embodiment, the term "application unit" refers to a supply module containing substances or mixtures of substances, in particular plastic granulates, color pigments or added substances (additives). Based on another embodiment, the term "application unit" refers to a filter module by means of which the filter pressure test can be conducted.

The term "automatically replace" in this context refers to the position (at least relative to a removing system) into which application units are moved by means of the replacement system, in particular by pushing, pulling or turning, so that an application unit can be moved to the position of another application unit whilst the other application unit is being moved away from this position (simultaneously or successively) without a user having to touch or manually activate these application units.

The term "automatically replace" in the context of function means filling or emptying application units by means of the replacement system in a controlled manner so that an application unit can be filled or emptied independently of another application unit without a user having to touch or manually activate the relevant application units.

Based on one preferred embodiment, the replacement system comprises a holder system for holding the application units and a moving system (in particular having electric, mechanical, pneumatic or hydraulic moving units) for moving the application units. The apparatus also has a control unit for controlling the replacement system.

The replacement system is preferably configured to move a belt incorporating the application units or is configured to move application units in the form of containers or cartridges, and in particular is linear (optionally incorporating switch structures) and/or circular in shape (in particular in the form of a carousel or turntable). Another preferred option is one where the application units are arranged in several concentric positions for application units.

Based on one preferred embodiment, if the application units are provided in the form of cartridges, the replacement system may be configured to control operation of the application units instead of generating movement or in addition to generating movement or in addition to emptying individual cartridges or groups of cartridges in a defined manner, for example, in which case a "replacement" involves functionally activating a cartridge or a group of cartridges (e.g. initiating an emptying operation) and then activating another cartridge or another group of cartridges (e.g. initiating an emptying operation in particular whilst the first cartridge or group of cartridges is or are being closed again so that emptying no longer takes place there).

Based on one preferred embodiment, the apparatus is configured in such a way that the application units (e.g. cartridges) can be replaced during operation. This replacement can then be detected by the system, preferably automatically, e.g. by means of sensors, which measure the state of occupancy of the places provided for the application units or detect the removal/addition thereof, thereby enabling the partially processed materials to be tested or the filter modules to be constantly topped up by replacing the cartridges during ongoing operation. Application units that have been removed/added can be identified in particular by bar codes, other codes, electronic codes or transponders. In particular, sensors measure the level to which application units have been filled.

In one preferred embodiment, the system of application units comprises cartridges and is configured so that the cartridges are replaceable and can be removed or added, in particular by means of the replacement system.

The replacement system is preferably equipped to accommodate the application units (e.g. the cartridges) by means of its holder system and move them from one position to another. In this manner, the application units (e.g. cartridges) can be moved into a melt flow and moved back out of it or moved above a material inlet and moved away from it again. The holder system of the replacement system is preferably provided in the form of a disk and the application units (e.g. the cartridges) can be moved to the desired position by rotating and if necessary pushing the disk (carousel/turntable).

In one preferred embodiment, the apparatus is designed so that it is suitable for accommodating both cartridges and belts respectively incorporating application units.

In one preferred embodiment, the apparatus further comprises a storage unit designed for storing application units or filter modules or materials (e.g. granulates/pigments). Such a storage unit is preferably suitable for storing a filter belt which is unreeled step by step for a filter pressure test or for storing separate filter modules.

Based on another embodiment, the storage unit is preferably also designed to hold material granulate and supply it in a specific manner.

The storage unit is preferably also configured to condition the application units, filter modules or materials as required, in particular so that they are dried, cooled, heated or wetted.

In particular, the replacement system is also configured to move filter modules and/or materials out of the storage unit into an application unit (e.g. a cartridge) and move them outside and/or transfer an application unit from outside into the storage unit and/or move it from outside into an application unit and back out again.

In addition to the units described above, a preferred replacement system also has a transport system by means of which application units can be picked up, moved and dispensed again. The transport system preferably comprises elements from the group comprising grippers, electromagnets, rams, conveyor belts, rollers, suction units and blowers.

In one preferred embodiment, the apparatus comprises a marker unit and is configured to automatically identify the application units or the product of the machine, in particular by means of marks, bar codes, RFID elements, engraving or other patterns. To this end, the apparatus preferably has printers, marker elements, elements for applying adhesive materials, punches or other elements for altering surfaces.

In particular, the apparatus is configured to scan the application units or their markings by means of a scanning element and a computer unit equipped with operating software (in particular contained in the apparatus), and their position in the apparatus is determined on the basis of this scanned information or their position together with the scanned information is stored in a computer system. In this manner, the marking can be used to establish a clear correlation between the position of an application unit and its property or to obtain a specific disposition of application units in the apparatus.

In one preferred embodiment, the application units are disposed so that the respective adjacent application unit in one direction has a lower (or higher) value with respect to one of its properties. This enables a sequence of application units to be created.

In another preferred embodiment, the application units are marked by means of a coding system (e.g. bar code, RFID, colors), thereby enabling the aforementioned sequence to be created by any of these means, and/or the filter modules or materials present in the storage device or at least their places in the storage device are coded In one preferred embodiment, the correlation of the application units or the scanning operation involves transmitting information and the movement of the application units is controlled by means of a computer unit using control software.

In one preferred embodiment, the preferred apparatus is used as a filter pressure test apparatus and/or as a metering apparatus.

In one preferred embodiment, the apparatus is configured so that the melt can be supplied directly to one of the filter modules, in particular without an extruder and/or melt pump. As a result, the apparatus is suitable for in-line operation.

In another preferred embodiment, a plasticizer unit is provided, disposed upstream of the apparatus proposed by the invention in particular (in the form of metering apparatus or an "autosampler"). As a result, the apparatus is suitable for off-line operation.

A preferred filter pressure test apparatus comprises filter modules as application units and a sensor system for measuring pressure, and the filter modules can be positioned in the flow of the material melt (e.g. the plastic melt) and the replacement system is configured to automatically replace the filter modules.

A preferred filter pressure test method implemented by such an apparatus comprises the steps:

optionally pre-heating a filter module, automatically positioning a filter module (pre-heated if necessary) in the flow of a material melt, measuring the pressure in the material melt, in particular the pressure increase upstream of the filter module whilst extruding a defined quantity of material, automatically moving the filter module out of the material melt, optionally cooling the filter module, optionally discharging the filter module from the apparatus.

Suitable sensor systems are known to the skilled person and include in particular pressure sensors, which are disposed so that they are able to measure an increase in pressure upstream of the filter when a defined quantity of material is being extruded.

Preferred filter modules comprise filter-holder systems for screens/filters or for groups of screens/filters. Preferred filter modules comprise cartridges in which at least one filter/screen is disposed or the filter modules are disposed on belts (e.g. filter or screen belts) and correspond in particular to surfaces on these belts.

Preferred filter modules comprise screens and/or filters or combinations of filters and/or screens. Furthermore, preferred filter modules are regions of a screen or filter belt. As filter modules, it is preferable to use granulates, perforated surfaces or surfaces incorporating threads, belts, yarns and fibers, or fleeces made from minerals, plastics, metals or glass.

The replacement system is preferably configured to move a belt incorporating the filter modules through the melt flow or is configured to move cartridges in and out of a melt flow.

The filter modules are moved into the measuring area and back out of it by means of the replacement system. To this end, the apparatus preferably comprises an opening which is opened for this purpose and then closed again when a filter module has been introduced. The opening is preferably moved by electrical, mechanical, hydraulic means or by compressed air. In a preferred embodiment, the opening is opened, the holder systems of the replacement system are moved (e.g. by means of wedges and spindle drives), the filter module is moved into position and the opening closed again.

A preferred configuration is one with several concentric positions of filter modules. This enables filters/screens and packets of filters or screens of differing thickness to be inserted in a specific order.

Based on another preferred embodiment, the filter modules are areas on a belt-shaped screen or filter material.

It is preferable to use belts with screen/filter structures selected from the group comprising woven or knitted screens/filters, glass fiber screens/filters, lasered, calendared or needled screens/filters, metal foils incorporating orifices, fleeces (e.g. staple fiber fleeces) or combinations of the aforementioned structures next to one another and/or one on top of the other.

In one preferred embodiment, the replacement system is configured so that its holder system is able to receive a reeled filter module belt in a first position, and its moving system is configured so that it can unreel the belt and direct regions of the belt (where the filter modules are disposed) through a melt flow. The holder system is also preferably configured to receive the belt fed through the melt flow again and the moving system is configured to reel the belt again, optionally after curing, in which case the apparatus may be equipped with an additional cooling module for this specific purpose.

It is of advantage if the filter module is disposed in a pressure-tight arrangement in its measuring position so that the melt is not able to escape sideways.

The filter modules (even if on belts) preferably have a denser structure at their edges. Such a structure may be obtained using a denser weave/knit or a specific shape with a lesser density of holes at the edges for example. Such filter modules improve the sealing capacity of the apparatus.

Based on one preferred embodiment in this respect, the filter modules used are disposed on webs in particular. By using different web types, e.g. of differing fineness, these filter modules are provided as separate modules or in the form of successive and/or adjacent areas on a belt surface. The important thing here is that in order to provide a seal against the polymer melt, the screen webs are more densely woven lengthways and sideways along the peripheral regions of the filter modules than at the center of the filter modules.

In one preferred embodiment, sealing is achieved by means of metal foils, resins or other thermoplastic materials or thermosetting plastics, silicones, fluoropolymers (e.g. Teflon) that are resistant to high temperature and the respective material is applied to or on the peripheral regions of the filter modules.

It is preferable if the filter modules (especially if disposed on a belt) are such that in the peripheral region of the filter module, an edge with a width of 1 mm to 5 cm, in particular a width of between 5 mm and 2 cm, is provided which is specifically designed to improve sealing and has a denser filter/screen structure and/or a sealing compound surrounding a screen/filter area specifically provided for taking measurements.

Using the filter pressure test apparatus, it is possible to measure not only filter modules with one screen geometry but also to successively measure a number of filter modules which differ in terms of their fineness, screen type or screen materials. Similarly, it is possible to put together individual screen packets or take measurements using filter modules containing filter sands (e.g. comprising minerals, plastics and/or metals) and combinations of all possible materials.

With an embodiment of the type which enables filter modules to be replaced, not only is it possible to test materials on an automated basis, it is also possible to optimize the type of screens/filters used for the specific application. For example, it would be conceivable to use belts with a reinforced weave at the edges or with different weave structures along the length.

Accordingly, it is possible to find the right filters for the specific production process. For example, in the case of an inline filter pressure test set up in the side branch of a production machine or recycling machine, for example, it is possible to use the measurements from the filter pressure test or from downstream inline processes to set up the right filter geometry in the production or recycling machine automatically in order to ensure optimum material properties.

Based on one preferred embodiment, the apparatus comprises a tempering system configured to pre-heat the filter modules upstream of the measurement area and/or provide cooling after the measurement. After having been ejected, the filter modules are preferably cooled and drop in an orderly manner into a magazine and are optionally separated. This enables the screens to be used for further testing for impurities.

In order to obtain a constant throughput of the molten material, a melt pump and/or a measuring system for measuring the flow quantity (e.g. a system for measuring mass flow rate based on the Coriolis effect) is preferably provided between the extruder/screw conveyor and filter. If using a measuring system to measure the flow rate, a correct and constant throughput is preferably obtained by controlling the movement of the melt (e.g. the speed of the screw in the extruder).

As an alternative to the melt pump, another option is to use a special downstream melt extruder with a pressure-generating screw geometry.

As another alternative, however, the screw in the main extruder can be provided with appropriate geometries for building up pressure in the output region, e.g. special screw pitches.

Based on one preferred embodiment, the apparatus comprises at least one preliminary filter. This is of advantage in terms of protecting the apparatus, especially if raw materials with coarser impurities are being measured, e.g. metal particles, small stones, wood. In this context, the preliminary filter should be set up so that it does not affect the measurement result to any significant degree. In particular, the apparatus is configured so that this filter can also be automatically replaced (preferably by means of the replacement system).

A measurement method can be improved if the removed filter modules, which may contain important information in the material that has been filtered out, is sent for further testing, e.g. optical evaluation, tests under the microscope, spectroscopy (e.g. optical or IR) or ashing.

Based on a preferred embodiment, the filter modules are arranged so that when being replaced, they follow one another through the melt flow with increasing or decreasing values of a specific property. For example, the filter modules are arranged so that the next filter module in one direction respectively has a smaller (or larger) width of mesh/holes. This results in a sequence in which a measurement can be used to measure grades of the material melt in stages (e.g. degree of purity).

Based on one preferred embodiment, the apparatus is configured so that it is not the entire melt flow that is measured and instead, a part of the melt flow is diverted and measured in the context of a filter pressure test. This part is then preferably returned to the melt flow again. In particular, a sample is removed from the region of the conveyor screw or after the conveyor screw. The timing of the measurement taken for the filter pressure test is therefore effective because the manufacturing process does not have to be interrupted. In principle, all types of single-screw or multi-screw extruders, compounders, kneaders (co-rotating and counter-rotating, cylindrical and conical geometries) can be used as processing devices.

However, it is also preferable to test a melt from a piston container. In principle, the apparatus can also be used on a plasticizer unit of an injection casting machine.

A preferred metering apparatus comprises supply modules as application units, and the supply modules are disposed so that they are positioned or can be positioned above the material inlet of the system for mixing or melting materials and the replacement system is configured to automatically replace the supply modules in terms of this position and/or with respect to their function and empty their contents or a part of their contents into the material inlet of the system for melting or mixing materials.

A replacement in terms of position in this instance involves moving the relevant supply module or moving the replacement system relative to the supply module. A replacement in terms of their function in this instance involves controlling the emptying operation or stopping the emptying operation.

A preferred metering method using such an apparatus comprises the steps:
optionally: automatically positioning at least one supply module above the material inlet of the system for mixing or melting materials, or positioning a removing device accordingly in the case of fixed supply modules,
automatically opening the at least one supply module so that its contents or at least a part of its contents can be emptied into the material inlet of the system for mixing or melting materials, optionally by means of a metering element (e.g. a metering screw, a metering disk or a ram), optionally measuring the removed quantity and automatically closing the at least one supply module, and/or
automatically emptying the at least one supply module by means of suction,
optionally: automatically moving this supply module away from the material inlet of the system for mixing or melting materials or moving the removing device away in the case of fixed supply modules,
optionally: automatically emptying another supply module by means of the aforementioned steps.

Preferred supply modules comprise structures for receiving materials and material outlets which can be automatically opened and closed. Preferred supply modules comprise cartridges in which at least one material or material mixture can be placed or the supply modules are provided on belts (e.g. conveyor belts) and in particular correspond to surface elements on these belts.

The supply modules are preferably opened and closed electrically, mechanically, hydraulically or with compressed air. In the case of one preferred embodiment, the supply module is moved into position, the opening opened and after a predefined time, the opening is closed again.

It may also be preferable for the contents of a supply module to be emptied by means of suction.

Based on one preferred embodiment, a correctly metered quantity of respective material is removed from a supply module or a group of supply modules simultaneously or successively by means of the metering element (e.g. metering screw, metering disk or ram) and moved directly or via conveyor elements into the extruder. In particular in this instance, one supply module contains a base material for the product to be manufactured and other supply modules contain additional substances such as dyes, for example. In this manner, many different combinations of mixtures can be made up automatically under the control of a computer.

In the case of this embodiment, the supply modules are preferably not attached to the extruder but are merely connected to it via the conveying elements and the conveying elements (e.g. passages, hoses or conveyor belts) are configured to direct materials from the supply modules into the extruder.

In another preferred embodiment, at least one group of supply modules is mounted above an intake system (e.g. a hopper), in which case there is no need for the supply modules to be moved but the opening/closing of the supply modules must be controlled and the supply modules do not have to be replaced in terms of their location but with respect to their function (emptying).

Preferred supply modules contain materials in the form of powders, granulates, liquids or gels or mixtures of films, molded parts, pipes, sections, production residues and waste and scraps thereof.

The apparatus preferably comprises units for shaving or planing material from solid bodies.

In one preferred embodiment, the metering apparatus comprises, in particular for at least one or for every supply module, a measuring unit for measuring the quantity of material that has been removed or dispensed. Preferred units are volumetric and/or gravimetric measuring units, units for measuring the dispensing time or length of the dispensed material.

With such measuring units, it is possible to charge a machine with a clearly and exactly defined quantity of a material.

The replacement system is preferably configured to move supply modules disposed on a belt to a material inlet of a machine or is configured to move cartridges to this material inlet and then move them away again.

Also preferred is a design with several concentric positions of supply modules. Accordingly, different materials can be introduced into a machine in a specific order.

In one preferred embodiment, the replacement system is configured so that its holder system comprises supply modules (in particular in the form of cartridges or tanks), and at least one supply module preferably contains a flushing material for cleaning the machine.

Using the metering apparatus, it is possible not only to produce a single product from a single material mixture but also to produce several products from different material formulas on an automated basis or a single product on which regions of different material formulas adjoin one another. When manufacturing a product, it is also possible to measure it and the material formula can be changed in the event of a deviation from predefined measurement parameters in order to ensure that the quality of the product always conforms to an optimum standard.

Based on such an embodiment providing a replacement of supply modules, it is possible to test a material on an automated basis or produce test samples on an automated basis, in addition to offering the possibility of testing out automated formulas "overnight". To this end, the apparatus preferably has one of the marker units described above, which is configured to mark the test samples produced.

In one preferred embodiment, the supply modules are disposed so that they follow one another based on increasing or decreasing values of a specific property once a replacement has been completed. For example, the supply modules are disposed so that respectively adjacent supply modules in one direction contain different color pigments or plastic granulates of differing purity. In this manner, a sequence of test samples can be obtained that are directly correlated with one another.

Using the apparatus proposed by the invention enables a user to set up a manufacturing or measuring process to operate on an automated basis to the degree that a number of samples can be produced and/or measured without intervention on the part of the user and the results can be automatically logged, which makes the measurements very efficient.

In one preferred embodiment, the apparatus comprises the system for melting or mixing a material. Appropriate systems for melting or mixing materials are known to the skilled person. Preferred systems are mixing drums, blown film lines, continuous casting machines (casters), extruders, injection casting machines or screw conveyors.

In another preferred embodiment, the apparatus is provided in the form of an attachment for commercially available machines of this type. A system for running filter pressure tests can be equipped with a metering apparatus in the form of an attachment or a unit incorporating metering apparatus can be provided with a separately mountable filter pressure test apparatus or other testing devices, including modular testing devices.

Based on one preferred embodiment, at least one melt buffer is provided between the extruder head or conveyor screw and a measuring module or melt pump or between two measuring modules. This melt buffer collects inflowing melt and presses the melt out through an outlet as required. In this manner, a continuous measurement is possible, even when a system is being operated discontinuously.

Examples of preferred embodiments of the apparatus proposed by the invention are illustrated in the diagrams.

FIG. 1 illustrates a measuring device for a filter pressure test based on the prior art, as described above.

Figure 1:
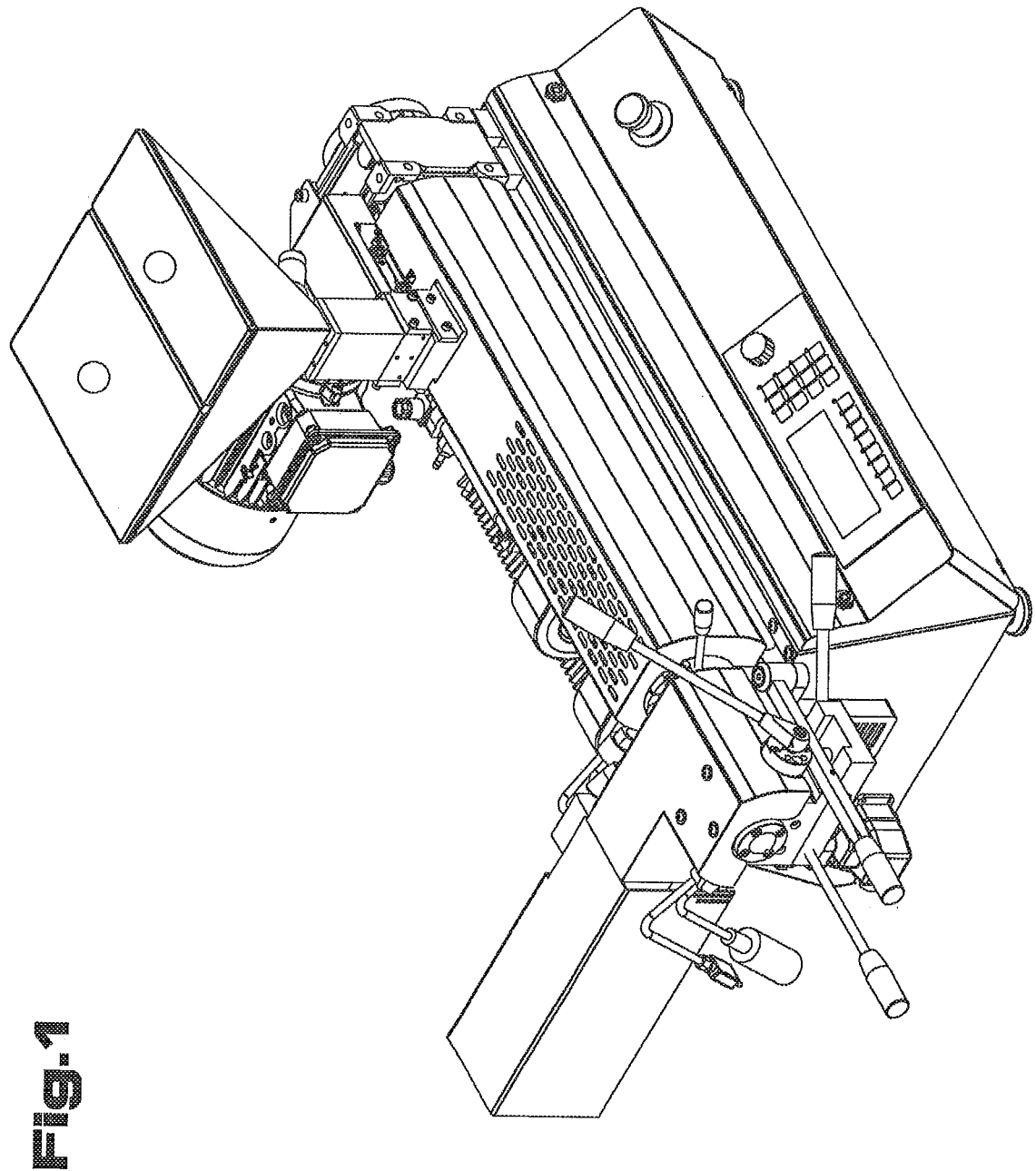
FIG. 1 is a schematic illustration of an embodiment based on the prior art.
Figure 2:
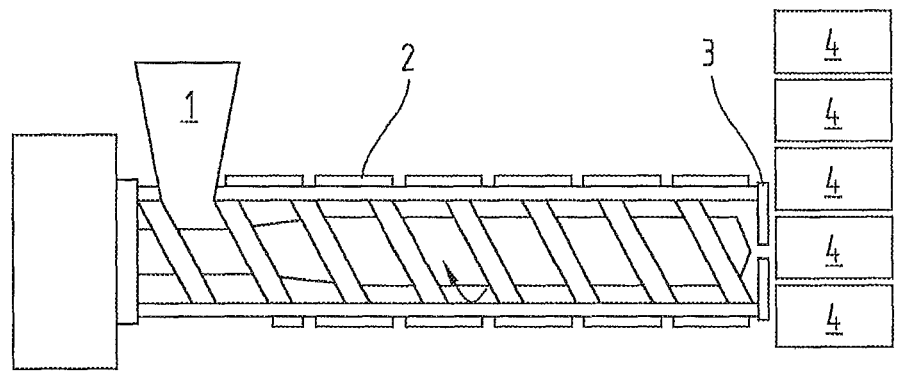
FIG. 2 is a schematic illustration of a preferred embodiment of a filter pressure test apparatus.

FIG. 2 is a schematic illustration of a preferred embodiment of the invention for measuring plastic products with a filter pressure test apparatus comprising a sensor system 1. In a filling unit, such as the illustrated hopper, a plastic granulate or plastic powder is fed into a screw conveyor and conveyed forwards through it to an outlet 3. During the passage through the screw conveyor 2, a plastic melt is formed and leaves via the outlet 3. Disposed in front of this outlet 3 is a row of cartridges 4, each of which contains a filter module. Although a linear layout of cartridges 4 was chosen for this diagram, a radial layout (turntable or carousel) is also preferred. The cartridges 4 can be moved automatically from the top down or from the bottom up by means of a replacement system, although this is not illustrated here.

Figure 3:
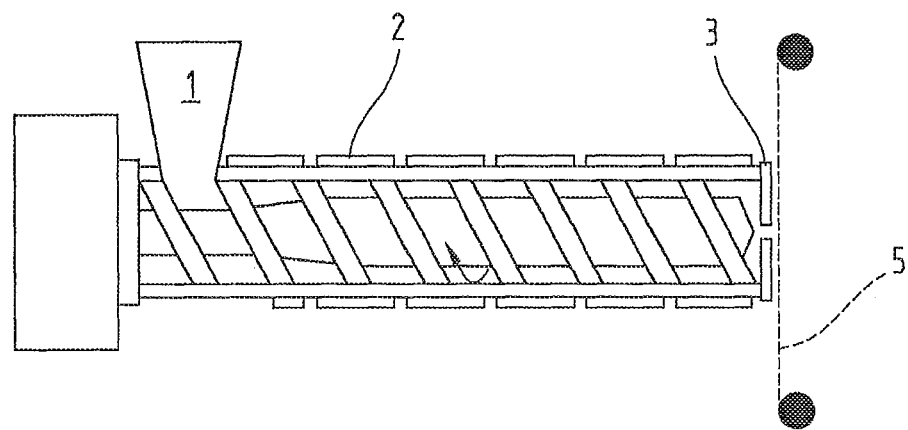
FIG. 3 is a schematic illustration of another preferred embodiment of a filter pressure test apparatus.

FIG. 3 is a schematic illustration of a preferred embodiment of the invention for measuring plastic products with another filter pressure test apparatus. Here too, a plastic melt is produced by means of the machine described above and leaves via the outlet 3. By contrast with FIG. 2, however, cartridges are not used for filter pressure testing but rather a belt 5 which is reeled in front of the outlet 3 and is moved up or down by a length for every measurement by means of the sensor system 1.

Figure 4:
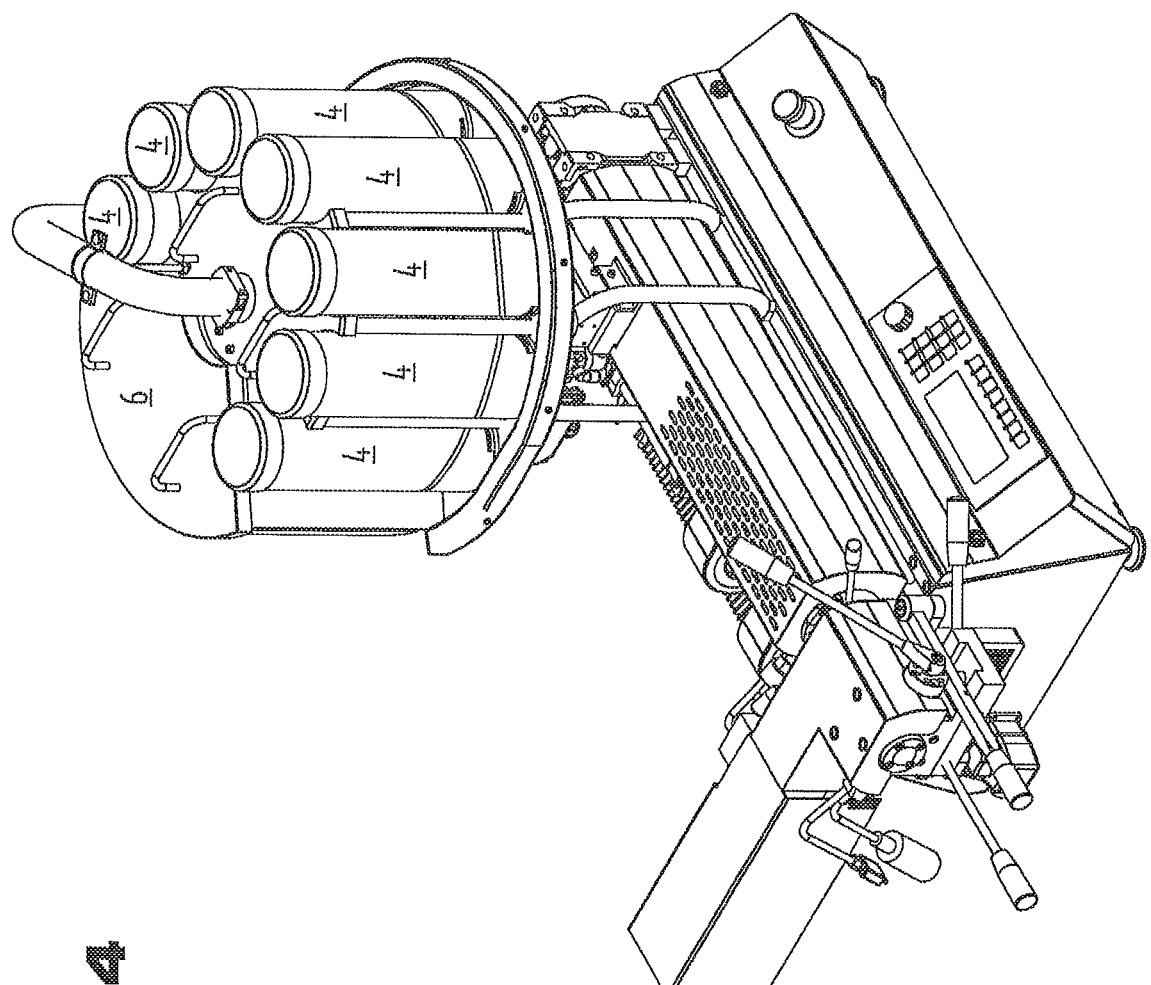
FIG. 4 is a schematic illustration of a preferred embodiment of a metering apparatus.

FIG. 4 is a schematic illustration of a preferred embodiment of a metering apparatus on an extruder for manufacturing plastic and is configured so that it can be filled with substances via its material inlet. It comprises supply modules in the form of cartridges 4 which are disposed on a round surface in the form of a circle segment. In addition, another supply module is provided in the form of a tank 6 containing a cleaning product and completes the circuit. The supply segments are rotatable and can be individually positioned above the hopper of the machine where its contents can be completely or partially emptied by means of a replacement system.

Figure 5:
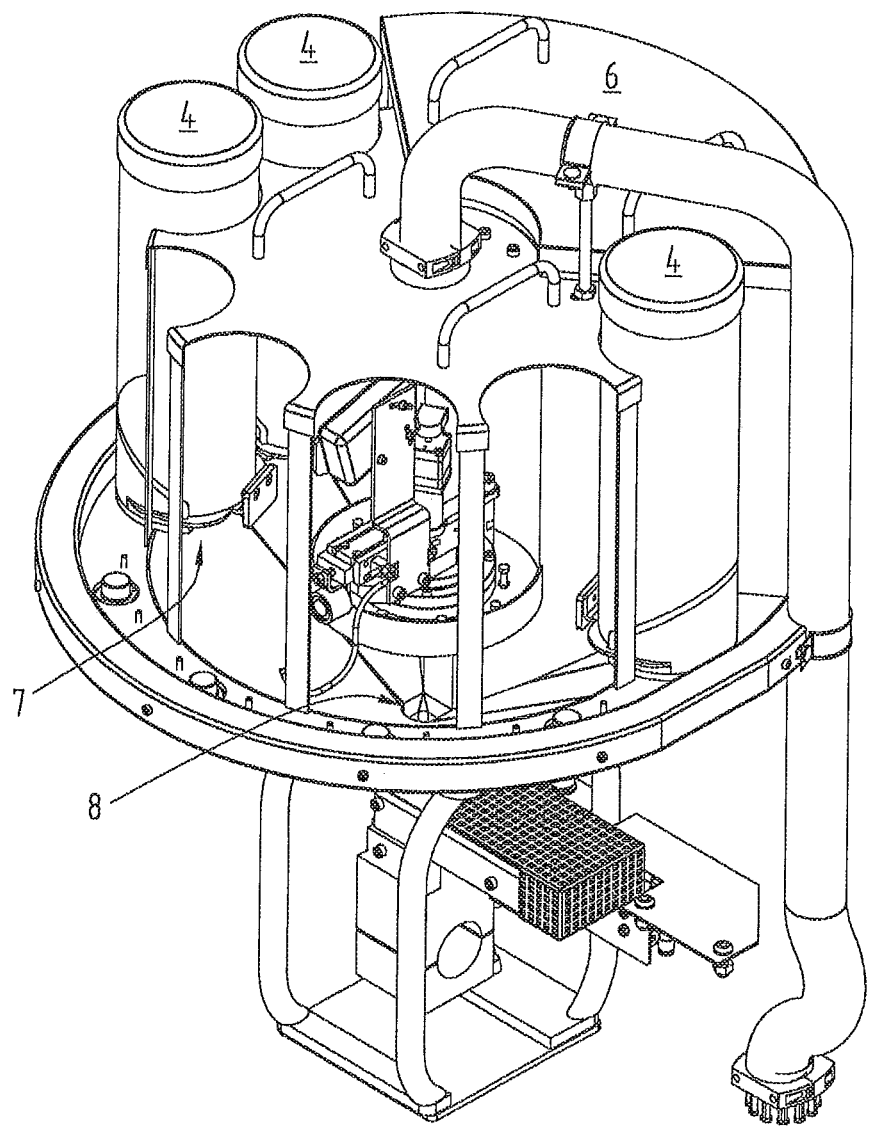
FIG. 5 is a schematic illustration of a detail of a metering apparatus.

FIG. 5 is a schematic illustration of a detail of the metering apparatus used in FIG. 4. In this instance, a cut-away view of the tank 6 and one of the cartridges 4 is illustrated. By means of the cartridge opening 7, which can be automatically opened as and when necessary, the contents of the relevant cartridge, e.g. a plastic granulate, color pigments or additives, drop down and are directed via the funnel-shaped intake unit 8 through the material inlet of the machine.

The embodiments illustrated as examples represent possible variants of the invention, and it should be pointed out at this stage that the invention is not specifically limited to the variants specifically illustrated, and instead the individual variants may be used in different combinations with one another and these possible variations lie within the reach of the person skilled in this technical field given the disclosed technical teaching.

Furthermore, individual features or combinations of features from the different embodiments illustrated and described may be construed as independent inventive solutions or solutions proposed by the invention in their own right.

The objective underlying the independent inventive solutions may be found in the description.

All the figures relating to ranges of values in the description should be construed as meaning that they include any and all part-ranges.

Above all, the individual embodiments of the subject matter illustrated in the drawings constitute independent solutions proposed by the invention in their own right. The objectives and associated solutions proposed by the invention may be found in the detailed descriptions of these drawings.

For the sake of good order, finally, it should be pointed out that, in order to provide a clearer understanding of the structure, some parts in the drawings are illustrated to a certain extent out of scale and/or on an enlarged scale and/or on a reduced scale.

LIST OF REFERENCE NUMBERS

1 Sensor system
2 Screw conveyor
3 Outlet
4 Cartridge
5 Belt
6 Tank
7 Cartridge opening
8 Intake unit

The invention claimed is:

1. An apparatus for manufacturing and testing workpieces, comprising
 a system for mixing or melting materials having a material inlet and a material outlet,
 a pressure filter test device comprising application units in the form of filter modules, a sensor system for measuring pressure and a replacement system, wherein the filter modules can be positioned in the flow of the material melt, the replacement system being configured to automatically replace the filter modules in respect of the position thereof, and the pressure filter test device can be connected or is connected fixedly to the material outlet of the system for mixing or melting materials, and
 a dispensing device comprising application units in the form of supply modules and a replacement system, wherein the dispensing device can be connected or is connected fixedly to the material inlet of the system for mixing or melting materials, which supply modules are disposed so that they are positioned or can be positioned above the material inlet of the system for mixing or melting materials, and the replacement system is configured to automatically move the supply modules or move the replacement system relative to the supply modules or empty the contents or a part of the contents of the supply modules into the material inlet of the system for melting or mixing materials.

2. The apparatus according to claim 1, wherein the replacement system of the dispensing device comprises a holder structure for holding the supply modules, a moving system for moving the supply modules and a control unit for controlling the replacement system of the dispensing device.

3. The apparatus according to claim 2, wherein the replacement system of the dispensing device is configured such that its holder structure comprises supply modules in the form of cartridges or tanks.

4. The apparatus according to claim 1, wherein the dispensing comprises a marker unit which is configured to automatically identify the supply modules by marks, bar codes, RFID elements, engraving or other patterns, and the dispensing device is configured to scan markings on application units by a scanning element and a computer unit configured with operating software, and their position in the dispensing is determined on the basis of this scanned information or their position together with the scanned information is stored in a computer system.

5. The apparatus according to claim 1, wherein the supply modules comprise structures for receiving materials and material outlets which can be automatically opened and closed, wherein the supply modules comprise cartridges in which at least one material or material mixture can be placed or the supply modules are provided on belts or the apparatus comprises a suction unit.

6. The apparatus according to claim 1, wherein the supply modules contain materials in the form of powders, granulates, liquids or gels or mixtures of films, molded parts, pipes, sections, production residues and waste and scraps thereof.

7. The apparatus according to claim 1, wherein the dispensing comprises, for at least one or every supply module, a measuring unit for measuring the quantity of material that has been removed or dispensed.

8. The apparatus according to claim 1, wherein the pressure filter test device comprises a storage unit configured for storing filter modules, and this storage unit is configured to store a roller of a filter belt or separate filter modules, and the storage unit is configured to condition filter modules as required so that they are dried, cooled, heated or wetted.

9. The apparatus according to claim 8, wherein the replacement system of the pressure filter test device is configured to move filter modules out of the storage unit into an application unit or move them outside or transfer an application unit from outside into the storage unit or move it from outside into an application unit or back out again.

10. The apparatus according to claim 1, wherein the filter modules comprise filter-holder systems for screens/filters or for groups of screens/filters.

11. The apparatus according to claim 1, wherein the filter modules are regions of a belt-shaped screen or filter material.

12. The apparatus according to claim 1, wherein the filter modules have a denser structure at their edges than at their center, and such a structure may be achieved using a denser weave/knit or a specific shape with a lesser density of holes at the edges, or the seal is achieved by metal foils, resins or other thermoplastic materials or thermosetting plastics that are resistant to high temperature, and the respective material is applied to or on the peripheral regions of the filter modules.

13. The apparatus according to claim 1, wherein the pressure filter test device comprises a tempering system configured to pre-heat the filter modules upstream of the measurement area or provide cooling after the measurement and, after having been ejected, the filter modules are cooled and dropped in an orderly manner into a magazine and are separated.

14. The apparatus according to claim 1, wherein the pressure filter test device is configured so that it is not the entire flow that is measured and instead, a part of the melt flow is diverted and measured in the context of a filter pressure test.

15. The apparatus according to claim 3, wherein the at least one supply module contains a flushing material for cleaning the machine.

\* \* \* \* \*